United States Patent [19]

Bauer

[11] Patent Number: 4,460,684
[45] Date of Patent: Jul. 17, 1984

[54] ASCORBATE-RESISTANT BROAD RANGE GLUCOSE TEST COMPOSITION, TEST DEVICE AND METHOD

[75] Inventor: Robert Bauer, Bristol, Ind.

[73] Assignee: Miles Laboratories, Inc., Elkhart, Ind.

[21] Appl. No.: 404,445

[22] Filed: Aug. 2, 1982

[51] Int. Cl.³ .............. C12Q 1/28; C12Q 1/54; G01N 33/66
[52] U.S. Cl. ........................... 435/14; 435/28; 435/805; 436/904
[58] Field of Search .............. 436/66, 904, 95; 435/14, 28, 805

[56] References Cited

U.S. PATENT DOCUMENTS

| | | | |
|---|---|---|---|
| 3,886,045 | 5/1975 | Meiattini | 435/28 X |
| 4,098,574 | 7/1978 | Dappen | 436/95 X |
| 4,119,405 | 10/1978 | Lam | 436/95 X |
| 4,427,770 | 1/1984 | Chen et al. | 436/95 X |

Primary Examiner—Arnold Turk
Attorney, Agent, or Firm—Edward H. Gorman, Jr.

[57] ABSTRACT

A composition, test device and method for detecting the presence and/or determining concentration of glucose in a liquid test sample are disclosed. The composition is capable of determining glucose concentration over a broad range, e.g. 0 to about 5,000 milligrams (mg) of glucose per deciliter (dl) of test sample. Moreover, the composition is resistant to interference from the presence of ascorbate in the sample. The composition comprises glucose oxidase, peroxidase and, as an indicator capable of producing a detectable response in the presence of peroxidase and $H_2O_2$, a mixture of two compounds. One has the structure

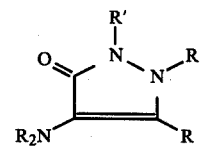

and the other has the structure

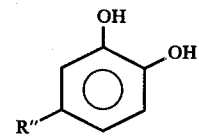

in which R, same of different, is H or lower alkyl, R' is aryl and R" is lower alkyl.

7 Claims, 3 Drawing Figures

ASCORBATE-RESISTANT BROAD RANGE GLUCOSE TEST COMPOSITION, TEST DEVICE AND METHOD

BACKGROUND OF THE INVENTION

1. Field of the Invention

The present invention relates to the field of analysis of a test sample for the presence of a reducing sugar, such as glucose. More particularly, it relates to a composition capable of producing a detectable response in the presence of the sugar. In addition to reducing sugars, the composition lends itself to the detection of hydrogen peroxide, peroxidase, peroxidatively active substances, hypochlorite and other analytes.

The analysis of test samples for the presence of sugars finds utility in many unrelated arts. Thus, the present invention pertains to such diverse pursuits as the brewing industry, biochemical research and medical diagnostics. In the brewing industry, for examples, starch is converted to sugars, such as maltose, prior to actual fermentation. The presence of maltose is therefore carefully monitored to assure high yields from the grain starting material. Many biochemical systems require glucose in carefully controlled concentrations as their cellular energy source, and the research of such systems necessitates that these concentrations be carefully monitored. The medical profession utilizes sugar analysis to a great extent in diagnosing and controlling such diseases as diabetes mellitus, which manifests itself by abnormally high glucose concentrations in the blood and urine.

Likewise many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances are also referred to herein as pseudoperoxidases. Peroxidatively active substances are enzyme-like in that they catalyze the redox reaction between peroxides and benzidine, o-tolidone, 3,3',5,5'-tetramethylbenzidine, 2,7-diaminofluorene or similar benzidine-type indicator substances, thereby producing a detectable response such as a color change. Most methods for determining the presence of occult blood in test samples rely on this pseudoperoxidase activity.

Thus, the field of the present invention extends to a very diverse assortment of pursuits. It finds applicability wherever sugar analysis becomes a matter of significance, be it in brewing, the food industry, scientific research or medicine. Moreover, it lends itself to a variety of techniques for determining the presence of a peroxidase or pseudoperoxidase. In fact, the present invention finds utility in any field where its unique propensity to exhibit a detectable response is adaptable. Any system which can ultimately provide $H_2O_2$ as a reaction product or which contains peroxidase or a pseudoperoxidase is suitable for application of the present invention, as are other systems such as swimming pool water containing hypochlorite and other strongly oxidizing systems.

2. Description of the Prior Art

The history of sugar analysis is perhaps most noteworthy because it has undergone dramatic change over the years, both in the basic chemistries utilized and in its format. For the most part these analyses can be characterized as oxidizing systems which, when reduced, initiate reaction conditions leading to a detectable response, such as a color change or change in wavelength of ultraviolet light absorbed or reflected by the system. Thus, reducing sugars will convert silver oxide to metallic silver and, if a solution of the sugar is applied to a piece of filter paper impregnated with silver oxide, a black dot develops. F. Feigl, Chem. Ind., Vol. 57, p. 1161, London (1938). Similarly, o-dinitrobenzene and the 3,4- and 3,5-isomers of dinitrophthalic acid give a sensitive color reaction (forming violet shades) when heated with reducing sugars in $Na_2CO_3$. T. Momose, et al., Chem. Pharm. Bull. Tokyo, Vol. 12, p. 14 (1964); F. Feigl, Spot Tests in Organic Analysis, 7th Edition, pp. 338–339, Elsevier Publ. Co., New York (1966).

But as early as 1849 it was known that reducing sugars would cause an alkaline solution of $CuSO_4$ to precipitate the yellow to red Copper(I)oxide (oxyhydrate). H. Fehling, Ann., Vol. 72 (1849). See also B. Herstein, J. Am. Chem. Soc., Vol. 32, p. 779 (1910). This early milestone, known as the Fehling test, lent impetus to the development of a far more sensitive test which utilized silver oxide in ammonia, the so-called Tollens reagents, which reacts readily with reducing agents to produce a black precipitate of metallic silver, often forming a mirror on the inside walls of glass reaction vessels. B. Tollens, Ber., Vol. 14, p. 1950 (1881); Vol. 15, p. 1635, 1828 (1882).

Because of the relatively high incidence of diabetes mellitus and its accompanying serious clinical consequences, high interest from the biological and medical professions arose in new techniques for analyzing glucose levels in urine and serum. This keen interest led to the development of several procedures which deviate dramatically from their solution chemistry forbears. These utilize sophisticated biochemical systems which can be incorporated into dry, dip-and-read devices, used in solution or suspension techniques, or in conjunction with spectrophotometers and other hardware.

Of these new techniques, one which lends itself especially well to sugar analysis is an enzymatic system wherein the analyte, for instance glucose, is a substrate for a particular enzyme, the reaction products being capable of eliciting a detectable response from a family of indicator compounds known loosely in the art as "benzidine-type indicators". These compounds can undergo color changes in the presence of hydrogen peroxide and the enzyme peroxidase. The glucose/glucose oxidase system exemplifies the prior art, wherein glucose is oxidized to gluconic acid with the concomitant formation of $H_2O_2$ in accordance with:

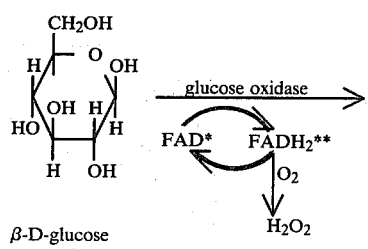

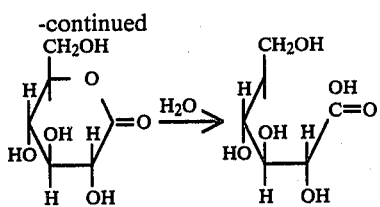

δ-gluconolactone      D-gluconic acid

*The coenzyme-flavin adenine dinucleotide
**Same, reduced form

It is the concomitant formation of hydrogen peroxide which facilitates the subsequent, indicator-related steps leading to observable color formation or other detectable response. Thus a benzidine-type indicator responds in the presence of hydrogen peroxide and peroxidase by changing its light absorptive capability.

In practice, this technology is presently utilized for glucose analysis in the form of dip-and-read reagent strips such as those marketed by the Ames Division of Miles Laboratories, Inc. under the trademark CLINIS-TIX® and others. Broadly, these comprise a plastic strip, at one end of which is mounted an absorbent paper portion impregnated with the appropriate enzymes, indicator compound and buffering agents as the principal active ingredients. They are used by dipping the reagent-bearing end into the test sample, removing it and comparing any color formed in the paper with a standard color chart calibrated to various glucose concentrations.

Several patents have issued which are deemed pertinent to the present invention with respect to its application to glucose analysis. U.S. Pat. No. 2,848,308, issued to Alfred H. Free, disclosed and claimed the basic enzyme chemistry whereby glucose oxidase, peroxidase and a benzidine-type indicator are used in a reagent strip to determine glucose in urine or other bodily fluid. U.S. Pat. No. 3,753,863, issued to Speck discloses the use of lower alkane polyols to "stabilize" indicator solutions of the benzidine type. U.S. Pat. No. 4,071,317, issued to Lam, discloses the stabilization of an occult blood-sensitive composition through the use of certain sulfone, sulfoxide and amide compounds as diluents during preparation of the composition. This latter composition comprises an organic hydroperoxide compound, and an indicator compound such as of the benzidine type.

Finally, U.S. Pat. Nos. 4,336,330 and 4,318,985, assigned to the assignee herein, deal with the determination of a broad range of glucose concentrations. This broad range capability is through the use of certain polymers in a reagent-bearing carrier matrix. Whereas the latter patent expressly teaches the use of crosslinked ureaformaldehyde resin, the former utilizes polystyrene. In neither of these patents, nor in the others mentioned above is there any mention of the presently claimed mixture for use as an indicator for measuring glucose. Nor is there mention of its resistance to ascorbate interference.

As in the case of sugar analysis, several methods for peroxidase or pseudoperoxidase analysis have evolved over the years which rely on enzyme-like catalysis of the oxidation of color-forming indicators in the presence of hydrogen peroxide. Primarily these include wet chemical procedures and "dip-and-read" type reagent-bearing strips. Of the former, a typical example is set forth in Richard M. Henry, et al., Clinical Chemistry Principles and Techniques, Hagertown, Maryland: Harper and Row (1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by most clinical assayists and analysts, utilizes "dip-and-read" reagent strips. Typical of such devices are reagent strips manufactured by the Ames Division of Miles Laboratories, Inc. and sold under the name HEMAS-TIX®. These comprise, in essence, a porous paper matrix affixed to a plastic strip or handle. The matrix is impregnated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semi-quantitative basis, the amount of unknown present in the sample.

The advantages of reagent strips over wet chemistry methods are predominantly twofold: strips are easier to use because neither the preparation of reagents nor the attendant apparatus is required; and greater stability of reagents is afforded, resulting in greater accuracy, sensitivity and economy.

As can be seen from the foregoing, the literature abounds with systems for measuring the presence and-/or concentrations of glucose in aqueous systems. There is however one serious problem inherent to many of these systems which renders them at least inconvenient, and at worst undependably inaccurate. The source of this problem is the presence of ascorbate ion in the test sample. For example, if the analysis to be performed is for glucose in urine, and the patients diet is high in vitamin C (ascorbic acid), the results of many of the prior art glucose tests will be falsely negative, or will give a reading lower than the actual concentration of glucose. This problem is caused by the propensity of ascorbic acid to reduce an indicator immediately upon its oxidation, thereby promoting a lag period during which color formation is retarded. Thus, if the glucose test depends upon the formation of color at a particular rate, the presence of ascorbic acid will diminish such rate thereby giving false lead lowered results. The present invention, on the other hand, provides a two-fold advantage over prior art systems. The present invention enables glucose analysis over an unusually broad range of concentrations, i.e., from 0 to about 5,000 mg/dl. At the same time, the system has surprisingly been found resistant to the adverse effects of ascorbic acid.

Another body of prior art exists which is pertinent to the present invention—that which deals with the reaction between 4-aminoantipyrine (hereafter 4-AAP) and phenolic compounds. It is known that a blue chromophor develops from the oxidative coupling of 4-AAP and chromotropic acid. Wong et al., Inter. J. of Biochem., 13, 159–163 (1981). Thus, 4-AAP is capable of coupling with chromotropic acid in the presence of peroxide to form a blue color. Also known is the detection of catechols through the use of 4-AAP to give a purplish color. LaRue et al., Anal. Chim. Acta., 31, 400–403 (1964). A recent reference dealing with the determination of phenol using 4-AAP cites the interference resulting from the presence of certain oxidants in the system. Among many oxidative ions mentioned is $H_2O_2$ as leading to false negative results. Norwitz et al., Analytical Chemistry, 51, 1632–1637 (1979). Finally, there is described a system utilizing 4-AAP and 3,5-dichloro-2-hydroxybenzenesulfonic acid in a direct enzymic assay for uric acid. Fossati, et al., Clinical Chemistry, 26, 227–231 (1980).

In the previous four references cited, which deal with 4-AAP and phenolic coupling agents, there is no mention of the analysis of glucose whereby a broad range of concentrations are detectable. Furthermore, the problem of ascorbate interference is in no way mentioned. The present invention deals squarely with both of these facets, and the end result is a broad range glucose test having dramatically minimal ascorbate sensitivity. Moreover, the Norwitz reference cited above indicates that the 4-AAP method of analysis is susceptible to error through the presence of oxidizing agents. It is speculated in the article that this caused by the oxidative decomposition of phenol.

To summarize the state of the art prior to the present invention, sugar-sensitive chemistries began to appear on the analytical scene as early as the middle of the 19th centruy with the advent of Fehling's solution and Tollens' reagent. Most of the "purely chemical" systems which have since emerged have been largely superseded by biochemical systems, particularly those which comprise a sugar oxidase, peroxidase and a peroxide-sensitive indicator of the benzidine type. Not only is it desirable to be able to measure glucose or other analyte over an extended concentration range, but it is equally necessary that the measured results not include inaccuracies due to the presence of ascorbic acid (Vitamin C) in the test sample. The present discovery enables the realization of both these desirable attributes.

SUMMARY OF THE INVENTION

Briefly stated, the present invention comprises a composition, test device and method for detecting the presence and/or determining concentration of glucose in a liquid test sample. The composition is capable of determining glucose concentration over a broad range, e.g. 0 to about 5,000 milligrams (mg) of glucose per deciliter (dl) of test sample. Moreover, the composition is resistant to interference from the presence of ascorbate in the sample. The composition comprises glucose oxidase, peroxidase and, as an indicator capable of producing a detectable response in the presence of peroxidase and $H_2O_2$, a mixture of two compounds. One has the structure

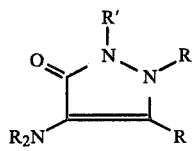

and the other has the structure

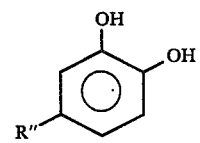

in which R, same or different, is H or lower alkyl, R' is aryl and R" is lower alkyl.

BRIEF DESCRIPTION OF THE DRAWINGS

FIGS. 1 and 2 portray the dramatic reduction of indicator fading from the reducing effects of ascorbate realized by the presence invention, as well as a remarkably enhanced rate of color formation. FIG. 3 demonstrates the accuracy of the present by described indicators in determining glucose.

DETAILED DESCRIPTION OF THE INVENTION

Figure 1:
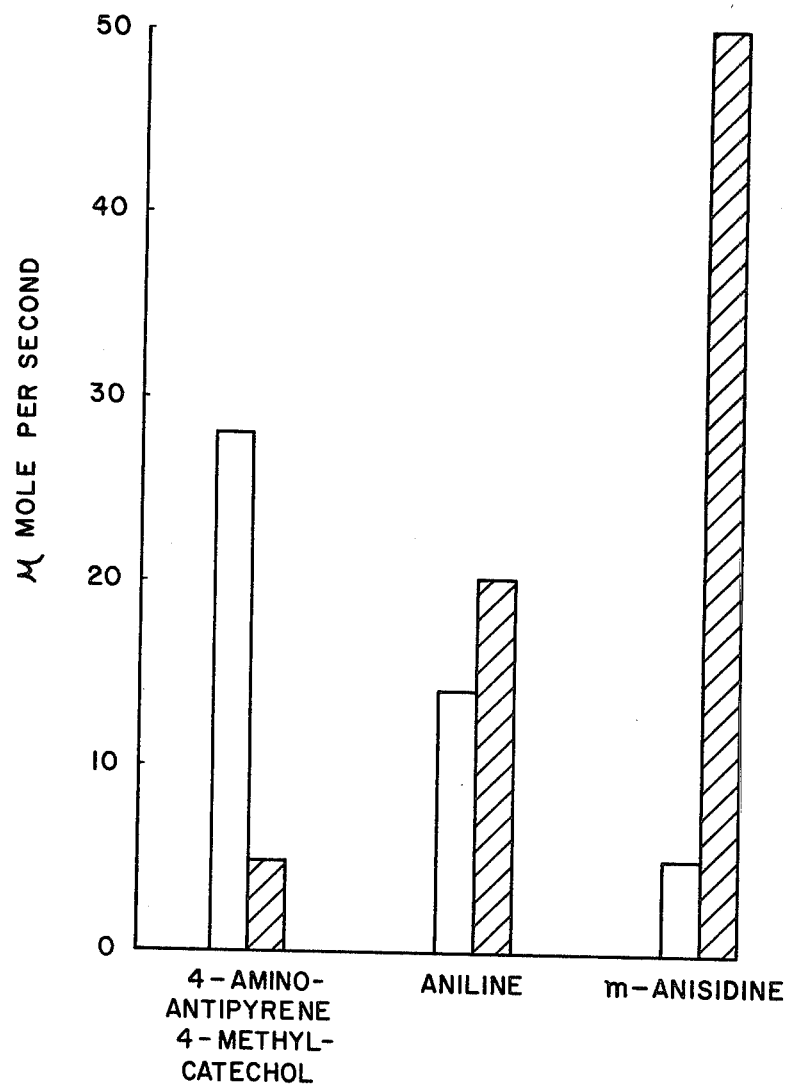
FIGS. 1–3 are provided to further illustrate the present invention. They are graphic portrayals of the data generated from Examples I–III, infra, respectively.

In the following discussion the terms, R, R' and R" are used in describing the compounds making up the indicator of the presently claimed composition. R includes H or lower alkyl. By "lower alkyl" is meant an alkyl group having 1 to about 6 carbon atoms. Included are such alkyl groups as methyl, ethyl, n-propyl, isopropyl, n-butyl, iso-butyl, tert-butyl, and the various isomers of pentyl and hexyl. These alkyl groups may be substituted or unsubstituted provided a particular substituent does not interfere with the detection of glucose.

Similarly, the term "aryl" refers to substituents of the 4-AAP structure which are aromatic in structure, i.e., which have a ring system characteristic of benzene and fused ring systems characteristic of phenanthrene, naphthylene and the like. As in the case of lower alkyl, aryl includes these aromatic groups in their substituted and unsubstituted forms provided that a particular substituent group not interfere with the glucose analysis reaction.

The composition comprises, in addition to the indicator, the enzymes glucose oxidase and peroxidase. The preferred peroxidase enzyme is horseradish peroxidase, although others are also effective in the invention. Glucose oxidase can be obtained from mycelia of fungi, such as Aspergilli and Penicillia, as well as from various commercial distributors.

The indicator is the key to the present invention in providing broad concentration range capability, while simultaneously exhibiting strong resistance to the adverse effects of ascorbate on the test results. It comprises a mixture of compounds, one of which is 4-AAP or a derivative thereof, the other being a 4-alkylcatechol.

The device of the present invention comprises a carrier matrix incorporated with the present composition to provide a tool for obtaining rapid, reliable results in glucose analysis. The carrier matrix is usually a porous substance such as filter paper. Other substances useful as a carrier matrix are felt, porous ceramic strips, woven or matted glass fibers, wood, cloth sponge material and argillaceous substances. Another alternative is a plastic surface, such as polystyrene film, on which the composition can be coated using suitable binders. All such carrier matrix materials are feasible for use in the present invention, as are others. Filter paper has been found to be especially preferred.

In forming the device, the composition is prepared as is indicated in the Examples infra, and then incorporated with an appropriate carrier matrix. For examples, where the preferred matrix material, filter paper, is employed, the paper is immersed in a solution of the composition, removed and dried. In another preferred embodiment, the composition—bearing paper is attached to one end of a polystyrene strip, the other end serving as a handle.

The device is used in practising the method of the invention by contacting it with a test sample suspected of containing glucose. In its strip mounted version, the filter paperbearing end is immersed in the test sample (for instance urine), removed, and observed for a response such as a change in color or percent light absorbance (or reflectance) at a particular wavelength. In the case where the appearance of, or change in, color is the detectable response, a comparative color chart can be used to obtain a semi-quantitative assay of glucose concentration by comparing the color developed by the device with the color chart blocks, each of which is the color developed by the device with standard glucose solutions of various known concentrations.

Most of the prior art "dip-and read" glucose test devices employ reagents capable of analyzing in a concentration range of 0 to 500 mg/dl. The present invention enables analysis in a range an order of magnitude greater, i.e., 0–5000 mg/dl. Moreover, whereas the prior art devices are sensitive to the presence of ascorbate, often producing false negative results, the claimed composition and device show an unexpected resistance to ascorbate. These advantages enable broad range semquantitative results which are dependable despite the presence of ascorbate in the test sample.

A preferred way of attaching the impregnated filter paper to a support, such as a polystyrene strip, is through the use of a double face adhesive tape. Particularly suitable is the product Double Stick marketed by the 3M Company. The filter paper can be attached to one side of the tape, the laminate trimmed to size, and mounted to one end of the plastic strip via the second adhesive side of the tape.

EXAMPLES

The following Examples are provided to further teach how to make and use the present invention. Preferred embodiments are described, and pertinent performance data is presented and analyzed. However, the Examples are meant as illustrative only, and are in no way intended as limiting the scope of the invention described and claimed herein.

Example I—Various Indicators

An experiment was performed to explore various indicators, including that of the present invention, in order to determine (a) the effects of ascorbate on their peroxide-catalyzed oxidation, and (b) the relative rates of color development. The data generated by the experiment shows that an indicator of the present invention 4-aminoantipyrine and 4-methylcatechol, are manyfold superior to aniline and m-anisidine in both respects. These results are dramatically evident in FIG. 1.

Equimolar amounts of the indicators were used in separate reagent solutions, the present invention indicator comprising 4-AAP and 4-methylcatechol (4-MC) in equimolar amounts, the sum being equal to the molar quantities of each of the other indicators. Thus each composition prepared contained the same reagents except for the indicator, and all compositions contained equimolar quantities of their respective indicators. The indicators used were 4-AAP/4MC, aniline and m-anisidine.

Three 1.0 ml cuvettes were charged with the following engredients and concentrations in distilled water to make 1.25 ml of solution.

| Ingredient | Concentration |
| --- | --- |
| Peroxidase (buffered at pH 5.5) | 30 μg/ml |
| Indicator | 2.0 mM |

Three solutions containing the above ingredients were prepared: the first containing 4-AAP and 4-MC as the indicator, each compound being present at a concentration of 1.0 mM; the second solution containing aniline at 2.0 mM; and the third containing m-anisidine at 2.0 mM.

Each solution was observed spectrophotometrically upon addition of sufficient $H_2O_2$ to make the solution 2.0 mM in $H_2O_2$, and the respective rates of color development were observed per unit time over a 2 minute interval.

After observation for color development reached 2 minutes following the addition of peroxide, sufficient ascorbate was added to make the solution 0.5 mM in ascorbate. The resultant mixture was then observed photometrically for the rate of decolorization due to reduction of the indicator by ascorbate. The rate data, expressed in μmole/sec., is as follows:

| Indicator | Rate of Color Development | Rate of Decolorization |
| --- | --- | --- |
| 4-AAP/4MC | 28 | 5 |
| Aniline | 14 | 20 |
| m-Anisidine | 5 | 50 |

The data is plotted in FIG. 1. As can be seen, the 4-AAP/4-MC indicator system demonstrated a faster color development rate and a slower ascorbate decoloring rate than did either aniline or m-anisidine. The irresitable conclusion is that 4-AAP/4-MC is dramatically more resistant to ascorbate interference, and provides a reliable, broad range test for glucose.

Example II—Various Phenolic Complexes

Figure 2:
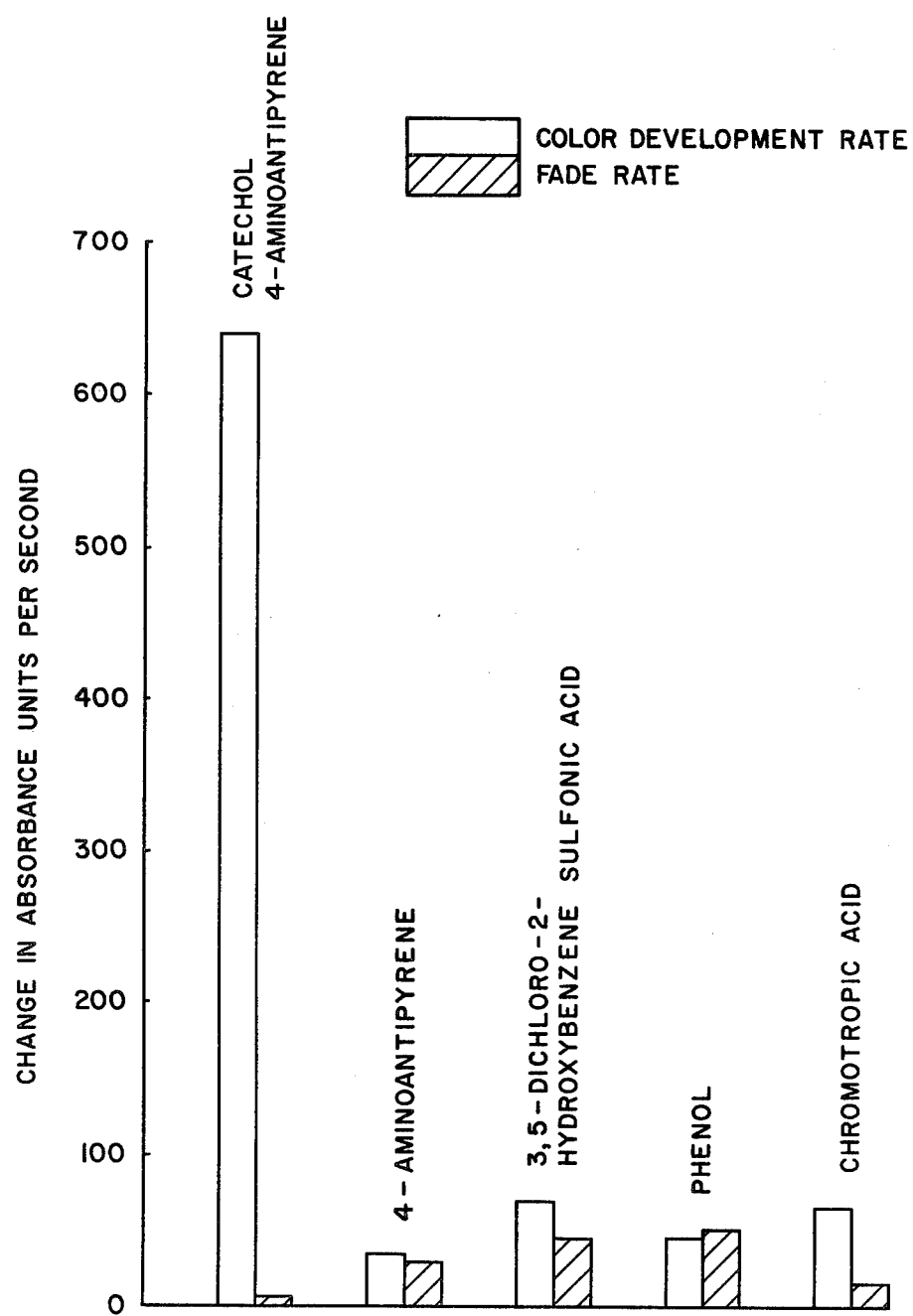

An experiment was conducted to compare the effects of various phenolic compounds on 4-AAP in the presence of $H_2O_2$ and peroxidase. The data obtained is plotted in FIG. 2 and shows that 4-MC, a compound of the present invention, far exceeds other phenolic derivatives in coacting with 4-AAP to produce faster color development and slower color fading due to the adverse effect of ascorbate.

Thus 4-AAP was oxidized by $H_2O_2$ and peroxidase, either alone or with various phenolic compounds, specifically phenol, chromotropic acid (CTA), 4-methylcatechol (present invention) and 3,5-dichloro-2-hydroxybenzene sulfonic acid (DHSA). The rate of color development was studied photometrically at a wavelength where the particular oxidized indicator exhibited strongest light absorbance. The rate of color formation was measured and compared to the rate of color formation in the absence of the phenolic compound. The data obtained was normalized by assuming the rate of color formation for 4-AAP alone to be equal to 1.00.

To each of five cuvettes was added an aqueous solution containing 10 mM of 4-aminoantipyrine. To four of the cuvettes was added sufficient phenolic compound to bring the concentration to 10 mM. Each solution was 0.311M in citrate and had a pH of 5.0. Horseradish peroxidase was added to give concentration of 50 mg/µl to 1 µg/ml, depending on enzyme activity. Then $H_2O_2$ was added to a final concentration of 10 mM. The relative rates of color development were measured and the resulting data normalized to the same enzyme concentration.

For each assay, when the optical density had reached 0.6, ascorbic acid was added rapidly to give a cuvette concentration of 200 µM, and the change in light absorbance measured. The data from the experiment is given in the following table, and is plotted in FIG. 2.

| Wavelength | Coupler | Relative Rate of Color Formation | ($\Delta A$/min) Reductive Rate With Ascorbate |
|---|---|---|---|
| 530 | none | 1.00 | 0.281 |
| 500 | 4-MC | 18.5 | 0.0599 |
| 520 | DHSA | 2.08 | 0.455 |
| 510 | phenol | 1.34 | 0.500 |
| 590 | CTA | 1.98 | 0.148 |

It is clear from the above that 4-methylcatechol forms color with aminoantipyrine many times faster than any other coupler studied and that the oxidized indicator color is more resistant to bleaching by ascorbic acid.

Example III—Preparation of Test Devices with 4-AAP/4-MC and with 2-Amino-8-naphthol-3,6-disulfonic acid An experiment was conducted whereby test devices for measuring a glucose were prepared. One set of devices contained as indicator 4-AAP and 4-MC; the other 2-amino-8-naphthol-3,6-disulfonic acid. Both indicator systems have about the same extinction coefficient.

A dip solution was prepared containing the following ingredients

| | |
|---|---|
| Polyvinyl pyrrolidone (15 g/ml in $H_2O$) | 2.0 ml |
| Polyoxyethylated oleyl alcohol (GAF Co. ON 870, 5 g/ml in $H_2O$) | 1.0 |
| Glucose oxidase (5000 U/ml) | 1.6 ml |
| Peroxidase (3 mg/ml in 1.0 M citrate buffer pH = 5.5) | 2.0 ml |
| 4-Methylcatechol (1.0 M in ethanol) | 1.0 ml |
| 4-Aminoantipyrine (1.0 M in ethanol) | 1.0 ml |
| Deionized water | 1.4 ml |
| Total volume | 10.0 ml |

A piece of Whatman 31ET filter paper was dipped in this solution and dried at 60° C. for 15 minutes.

Similarly, a test paper (device) was prepared from an identical solution except that 2.0 ml of 1M 2-amino-8-naphthol-3,6-disulfonic acid in ethanol was used instead of the 4-AAP and 4-MC.

Both devices were briefly immersed in glucose solutions of known concentrations, and incubated for 60 seconds. A second series of glucose solutions containing 50 mg/dl ascorbic acid was used to measure the affects of ascorbate.

Figure 3:
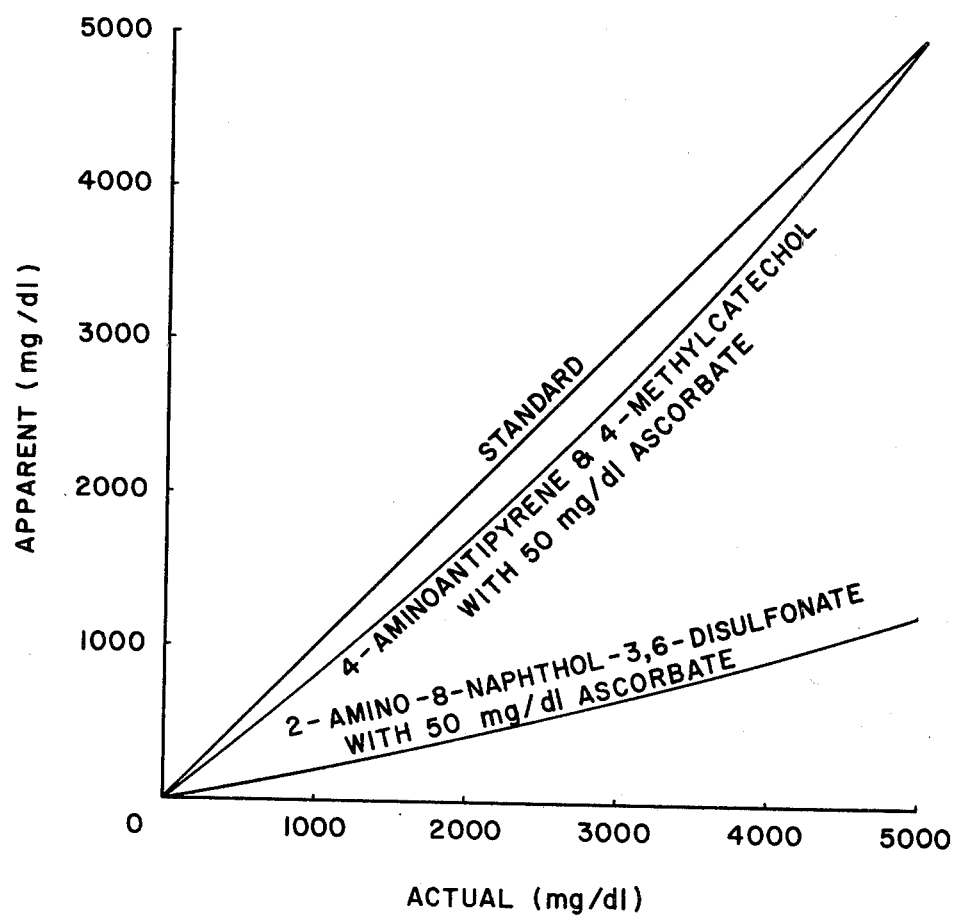

Devices from both sets were calibrated by dippint into the ascorbate-free glucose, incubating for 60 seconds and observing color formation. Next, the devices were studied in conjunction with the ascorbate-containing glucose solutions using the same procedure. The results are listed below and plotted in FIG. 3.

| Actual Glucose Con., mg/dl | Apparent Glucose, mg/dl | |
|---|---|---|
| | 4-AAP/4-MC | Aminonaphthol Disulfonate |
| 0 | 0 | 0 |
| 50 | 20 | 0 |
| 100 | 70 | Trace |
| 250 | 150 | 50 |
| 500 | 300 | 80 |
| 1000 | 800 | 200 |
| 2000 | 1500 | 500 |
| 5000 | 5000 | 1300 |

The results clearly indicate improved ascorbate resistance with the aminoantipyrine/methylcatechol reagent strip.

What is claimed is:

1. A composition for detecting the presence of glucose, determining the concentration of glucose, or both, in a test sample, whereby the composition is capable of determining concentration over a range of 0 to about 5000 milligrams of glucose per deciliter of test sample, and whereby the composition is resistant to interference from the presence of ascorbate in the sample, the composition comprising glucose oxidase, peroxidase and, as an indicator capable of producing a detectable response in the presence of peroxidase and $H_2O_2$, a mixture of two compounds, one having the structure

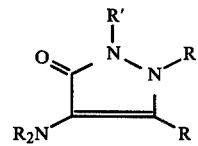

and the other having the structure

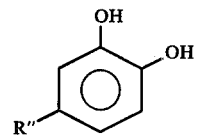

in which R, same or different is H or lower alkyl, R' is aryl and R" is lower alkyl.

2. The composition of claim 1 in which the compounds are 4-aminoantipyrine and 4-methylcatechol.

3. A test device for detecting the presence and/or determining the concentration of glucose in a test sample comprising a carrier matrix incorporated with the composition of claim 1 or 2.

4. The test device of claim 3 in which the carrier matrix is paper.

5. A method for detecting the presence and/or determining the concentration of glucose in a test sample comprising contacting the sample with the composition of claim 1 or 2, and observing a detectable response.

6. A method for detecting the presence and/or determining the concentration of glucose in a test sample comprising contacting the sample with the test device of claim 3 and observing a detectable response.

7. A method for detecting the presence and/or determining the concentration of glucose in a test sample comprising contacting the sample with the test device of claim 4 and observing a detectable response.

* * * * *